United States Patent
Hubbell et al.

(10) Patent No.: US 7,132,475 B2
(45) Date of Patent: Nov. 7, 2006

(54) BLOCK COPOLYMERS FOR MULTIFUNCTIONAL SELF-ASSEMBLED SYSTEMS

(75) Inventors: Jeffrey A. Hubbell, Zurich (CH); Alessandro Napoli, Zurich (CH); Nicola Tirelli, Uster (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 328 days.

(21) Appl. No.: 10/047,404

(22) Filed: Oct. 19, 2001

(65) Prior Publication Data

US 2003/0059906 A1    Mar. 27, 2003

Related U.S. Application Data

(60) Provisional application No. 60/241,561, filed on Oct. 19, 2000.

(51) Int. Cl.
C08K 5/372    (2006.01)
C08F 28/02    (2006.01)

(52) U.S. Cl. ............... 525/93; 525/118; 525/417; 526/286

(58) Field of Classification Search ............ 525/417, 525/118, 93; 526/286
See application file for complete search history.

(56) References Cited

U.S. PATENT DOCUMENTS

| | | | |
|---|---|---|---|
| 4,618,400 A | 10/1986 | Wood | |
| 5,268,305 A | 12/1993 | Ribi et al. | |
| 5,294,690 A | 3/1994 | Iguchi et al. | |
| 5,330,911 A | 7/1994 | Hubbell et al. | |
| 5,374,668 A * | 12/1994 | Kanemura et al. | 523/451 |
| 5,410,016 A | 4/1995 | Hubbell et al. | |
| 5,427,915 A | 6/1995 | Ribi et al. | |
| 5,446,090 A | 8/1995 | Harris | |
| 5,529,914 A | 6/1996 | Hubbell et al. | |
| 5,567,422 A | 10/1996 | Greenwald | |
| 5,573,934 A | 11/1996 | Hubbell et al. | |
| 5,575,815 A | 11/1996 | Slepian et al. | |
| 5,612,390 A | 3/1997 | Iguchi et al. | |
| 5,635,207 A | 6/1997 | Grinstaff et al. | |
| 5,648,506 A | 7/1997 | Desai et al. | |
| 5,702,717 A | 12/1997 | Han et al. | |
| 5,752,974 A | 5/1998 | Rhee et al. | |
| 5,801,033 A | 9/1998 | Hubbell et al. | |
| 5,817,840 A | 10/1998 | Nicolaou et al. | |
| 5,852,182 A | 12/1998 | Cook et al. | |
| 5,858,746 A | 1/1999 | Hubbell et al. | |
| 5,874,500 A | 2/1999 | Rhee et al. | |
| 5,880,131 A | 3/1999 | Greenwald et al. | |
| 5,897,955 A | 4/1999 | Drumheller | |
| 5,932,462 A | 8/1999 | Harris et al. | |
| 5,945,457 A | 8/1999 | Plate et al. | |
| 5,965,588 A | 10/1999 | Vasquez et al. | |

2003/0044468 A1    3/2003 Cellesi et al.

FOREIGN PATENT DOCUMENTS

| | | |
|---|---|---|
| GB | 1348045 A | 3/1974 |
| WO | WO 95/13312 | 5/1995 |
| WO | WO 97/22371 | 6/1997 |
| WO | WO 98/32466 | 7/1998 |
| WO | WO 99/14259 | 3/1999 |
| WO | WO 99/22770 | 5/1999 |
| WO | WO 99/34833 | 7/1999 |
| WO | WO 00/09087 | 2/2000 |
| WO | WO 00/44808 | 8/2000 |
| WO | WO 01/02017 | 1/2001 |
| WO | WO 01/92584 A1 | 12/2001 |

OTHER PUBLICATIONS

Baker, "Controlled Release of Biologically Active Agents," Bruck, ed., p. 84-131 John Wiley and Sons, New York (1987).
Ballini et al., "Amberlyst A-27, and Efficient Heterogeneous Catalyst for the Michael Reaction of Nitroalkanes with β-Substituted Alkene Acceptors," J. Org. Chem. 61:3209-3211 (1996).
Boyland et al., "Enzymes Catalysing Conjugations of Glutathione with Alpha-beta-unsaturated Carbonyl Compounds," Biochem. J. 109:651-661 (1968).
Chasseaud, "Distribution of Enzymes that Catalyse Reactions of Glutathione with Alpha beta-unsaturated Compounds," Biochem. J. 131:765-769 (1973).
Deutsch et al., "Synthesis of Congeners and Prodrugs. 3. Water-Soluble Prodrugs of Taxol with Potent Antitumor Activity," Journal of Medicinal Chemistry 32:788-792 (1989).
Dumitriu et al., "Polymeric Drug Carriers," In Polymeric Biomaterials, Dumitriu, ed., p. 435-449 and 466-724, Marcel Dekker, New York (1994).
Duncan et al., "Soluble Synthetic Polymers as Potential Drug Carriers," Adv. In Polym. Sci. 57:51-101 (1984).
Eisele et al., "Kinetics of Photocrosslinking Reactions of a DCPA/EA Matrix in the Presence of Thiols and Acrylates," J. Polym. Sci., Polym. Chem. Ed. 35:2333-2345 (1997).
Fan et al., "Molecular recognition and catalysis: incorporation of an 'oxyanion hole' into a synthetic receptor," New J. Chem. 21(1):81-85 (1997).

(Continued)

Primary Examiner—James J. Seidleck
Assistant Examiner—Olga Asinovsky
(74) Attorney, Agent, or Firm—Clark & Elbing LLP; Kristina Bieker-Brady

(57) ABSTRACT

The invention provides methods for the preparation of multiblock copolymers, dispersions of multiblock copolymers, vesicles and micelles containing multiblock copolymers, and oxidative degradation products of multiblock copolymers.

35 Claims, 14 Drawing Sheets

OTHER PUBLICATIONS

Friedman et al., "Relative Nucleophilic Reactivities of Amino Groups and Mercaptide Ions in Addition Reactions with α,β-Unsaturated Compounds," J. Am. Chem. Soc. 87(16):3672-3682 (1965).

Greenwald et al., "Drug Delivery Systems: Water Soluble Taxol-2'-Poly(ethylene glycol) Ester Prodrugs-Design and in Vivo Effectiveness," J. Med. Chem. 39:424-431 (1996).

Ghandehari et al., "In Vitro Degradation of pH-sensitive Hydrogels Containing Aromatic Azo Bonds," Biomaterials 18:861-872 (1997).

Hern et al., "Incorporation of adhesion peptides into non-adhesive hydrogels useful for tissue resurfacing," J. Biomed. Mater. Res. 39:266-276 (1998).

Hirai et al., "pH-induced Structure Change of Poly (vinyl alcohol) Hydrogel Crosslinked with Poly (acrylic acid)," Angewandte Makromolekulare Chemie 240-213-219 (1996).

Ishihara et al., "Tris(pentafluorophenyl) boron as an Efficient, Air Stable, and Water Tolerant Lewis Acid Catalyst," Bull. Chem. Soc. Jpn. 68:1721-1730 (1995).

Kawai et al., "New Application of Solid Acid to Carbon-Carbon Bound Formation Reactions: Clay Montmorillonite-Catalyzed Aldol Reactions of Silyl Enol Ethers with Aldehydes and Acetals," Bull. Chem. Soc. Jpn. 61:1237-1245 (1988).

Kito et al., "Biocompatible Coatings for Luminal and Outer Surfaces of Small-caliber Artificial Grafts," Journal of Biomedical Materials Research 30:321-330 (1996).

Lau et al., "Conjugation of Doxorubicin to Monoclonal Anti-carcinoembryonic Antigen Antibody via Novel Thiol-directed Cross-linking Reagents," Bioorganic & Medicinal Chemistry 3:1299-1304 (1995).

Lau et al., "Novel Doxorubicin-Monoclonal Anti-carcinoembryonic Antigen Antibody Immunoconjugate Activity in vitro," Biorganic & Medicinal Chemistry 3:1305-1312 (1995).

Mathur et al., "Methods for Synthesis of Hydrogel Networks: A Review," Journal of Macromolecular Science-Reviews in Macromolecular Chemistry and Physics C36(2):405-430 (1996).

Moghaddam et al., "Molecular Design of 3-Dimensional Artificial Extracellular-matrix: Photosensitive Polymers Containing Cell Adhesive Peptide," Journal of Polymer Science: Part A: Polymer Chemistry 31:1589-1597 (1993).

Morpurgo et al., "Preparation and Characterization of Poly(ethylene glycol) Vinyl Sulfone," Bioconjugate Chem. 7:363-368 (1996).

Pato et al., "Polymers containing enzymatically degradable bonds, 9$^{a)}$ Chymotrypsin catalyzed hydrolysis of a p-nitroanilide drug model, bound via oligopeptides onto poly(vinylpyrrolidone-co-maleic anhydride)," Makromol. Chem. 185:231-237 (1984).

Pathak et al., "Rapid Photopolymerization of Immunoprotective Gels in Contact with Cells and Tissue," Journal of the American Chem. Society 114:8311-8312 (1992).

Petka et al., "Reversible Hydrogels from Self-Assembling Artificial Proteins," Science 281:389-392 (1998).

Pitt et al., "Controlled Drug Delivery," In Biodegradation of Polymers, Basic Concepts, vol. 1, p. 53-80. CRC Press, Boca Raton, Florida (1983).

Romanowska et al., "Michael Additions for Syntheses of Neoglycoproteins," Methods in Enzymol. 242:90-101 (1994).

Sawhney et al., "Bioerodible Hydrogels Based on Photopolymerized Poly(ethylene glycol)-co-poly( α-hydroxy acid) Diacrylate Macromers," Macromolecules 26:581-587 (1993).

Tanaka et al., "Michael-type Addition of Illudin S, a Toxic Substance from *Lampteromyces japonicus*, with Cysteine and Cysteine-containing Peptides In Vitro," Chem. Pharm. Bull. 44:273-279 (1996).

West et al., "Comparison of Covalently and Physically Cross-linked Polyethylene Glycol-based Hydrogels for the Prevention of Postoperative Adhesions in a Rat Model," Biomaterials 16:1153-1156 (1995).

Wright et al., The Chemistry and Pharmacology of Taxol and Its Derivatives, Farina, ed., p. 110-130 and 165-300,, Elsevier, New York (1995).

Zalipsky et al., "Attachment of Drugs to Polyethylene Glycols," Eur. Polym. J. 19:1177-1183 (1983).

Zhao et al., "Novel Degradable PEG Esters for Drug Delivery: Synthesis and Characterization," Polymer Reprints 38:526-527 (1997).

Aida et al., "*Zinc N-substituted Porphyrins as Novel Initiators for the Living and Immortal Polymerizations of Episulfide,*" Macromolecules, 23:3887-3892 (1990).

Blume et al., "*Specific Targeting with Poly(ethylene glycol)-modified Liposomes: Coupling of Homing Devices to the Ends of the Polymeric Chains Combines Effective Target Binding with Long Circulation Times,*" Biochim. Biophys. Acta., 1149:180-184 (1993).

Booth et al., "*Effects of Block Architecture and Composition on the Association Properties of Poly(oxyalkylene) Copolymers in Aqueous Solution,*" Macromol. Chem. Rapid Commun., 21:501-527 (2000).

Discher et al., "*Polymersomes: Tough Vesicles Made from Diblock Copolymers,*" Science, 284:1143-1146 (1999).

Gabizon, "*Targeting Folate Receptor with Folate Linked to Extremities of Poly(ethylene glycol)-Grafted Liposomes: In Vitro Studies,*" Bioconjugate Chem., 10:289-298 (1999).

Inoue et al., "Gene Therapy of Human Bladder Cancer with Adenovirus-mediated Antisense Basic Fibroblast Growth Factor," Clinical Cancer Research, 6:4422-4431 (2000).

Lasic et al., ed. Stealth Liposomes, Chapters 2, 4, and 9, CRC Press: Boca Raton, FL, (1995).

Mortensen, "Block Copolymer in Aqueous Solution: Micelle Formation and Hard-sphere Crystallization," Prog. Colloid. Polym. Sci., 93:72-75 (1993).

Torchilin et al., "*Poly(ethylene glycol) on the Liposome Surface: on the Mechanism of Polymer-coated Liposome Longevity,*" Biochim. Biophys. Acta, 1195:11-20 (1994).

Watanabe et al., "First Example of Photoinduced Copolymerizability Enhancement, Copolymerization of Epoxide and Episulfide Initiated with Zinc N-substituted Porphyrin under Visible Light Irradiation," Macromolecules, 24:3970-3972 (1991).

Won, "*Giant Wormlike Rubber Micelles,*" Science, 283:960-963, (1999).

Yu et al., "Bilayer Morphologies of Self-assembled Crew-cut Aggregates of Amphiphilic PS-b-PEO Diblock Copolymers in Solution," Macromolecules, 31:3509-3518, (1998).

Zalipsky et al., "*Peptide Attachemnt to Extremities of Liposomal Surface Grafted PEG Chains: Preparation of the Long-circulating Form of Laminin Pentapeptide, YIGSR,*" Bioconjugate Chem., 5:705-708 (1995).

Zalipsky, "Long-circulating, Polyethylene Glycol-grafted Immunoliposomes,"J. Controlled Release, 39:153-161 (1996).

Greenwald et al "Camptothecin-20-PEG Ester Transport Forms: the Effect of Spacer Groups on Antitumor Activity" Bioorganic & Medicinal Chemistry 1998, 6:551-562.

Kopecek et al. "Controlled Release of Drug Model from N-(2-Hydroxypropyl)-methacrylamide Copolymers" Ann. N.Y. Acad. Sci. 1985, 446:93-104.

Pendri et al. "Antitumor Activity of Paclitaxel-2'-glycinate Conjugated to Poly(ethylene glycol): a Water-soluble Prodrug" Anti-cancer Drug Design 1998, 13:387-395.

* cited by examiner

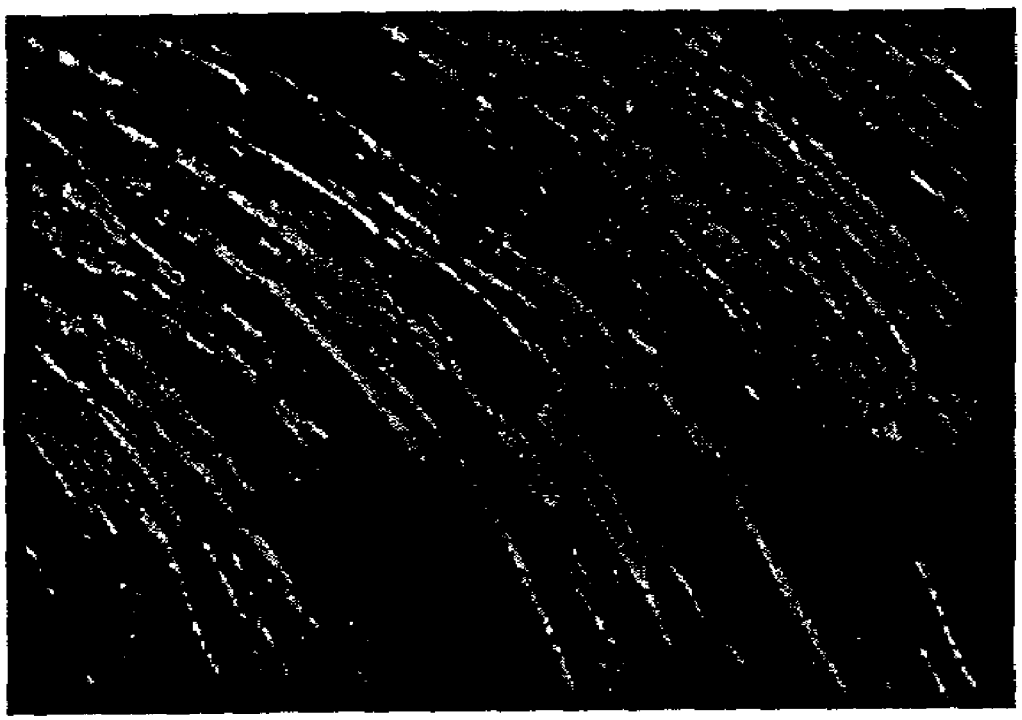
Figure 8, 10X picture

BLOCK COPOLYMERS FOR MULTIFUNCTIONAL SELF-ASSEMBLED SYSTEMS

CROSS-REFERENCE TO RELATED APPLICATIONS

This application claims benefit from co-pending U.S. Provisional application Ser. No. 60/241,561, filed Oct. 19, 2000, hereby incorporated by reference.

BACKGROUND OF THE INVENTION

Colloidal particles such as nanospheres, liposomes, and micelles have been studied extensively for site-specific drug delivery. Generally, such particles must escape capture by the reticuloendothelial system (RES) of the liver and the great filtration activity of the lungs if they are to deliver drugs to other tissues. In recent years, survival of colloidal systems in the blood has been improved by the use of PEG-containing amhiphiles (Lasic et al., Ed. *Stealth Liposomes*; CRC Press: Boca Raton, Fla., 1995). As a result of the PEG, macrophage clearance of PEG-based liposomes has been drastically reduced by decreasing opsonization by plasma proteins (Torchilin et al., *Biochim. Biophys. Acta* 1994, 1195, 11–20). Furthermore, a variety of ligands, such as antibodies, growth factors, and cytokines, have served to enhance the delivery capabilities of PEG-coated liposomes, and it has been demonstrated that the maximal activity is shown by ligands tethered to the distal end of PEG chains (Blume et al., *Biochim. Biophys. Acta* 1993, 1149, 180–184; Zalipsky et al., *Bioconjugate Chem.* 1995, 6, 705–708; Zalipsky, *J. Controlled Release* 1996, 39, 153–161; Gabizon, *Bioconjugate Chem.* 1999, 10, 289–298). Some of these ligands can lead to very efficient cellular uptake, such as the use of growth factors, for example, fibroblast growth factor to effect cellular uptake of DNA formulations.

SUMMARY OF THE INVENTION

Polymers with novel block structures, containing spatially separated hydrophobic and hydrophilic parts (hereafter called amphiphilic polymers), have been developed for applications in encapsulation of organic and inorganic matter and controlled delivery of bioactive compounds. These polymers are unique (a) in their preparation method, which allows the synthesis of diblock, symmetric and asymmetric triblock, multiblock, star, or dendritic copolymers and the presence of sensitive biological materials in at least one of the blocks; (b) in their preparation of self-assembled structures, ranging from micelles to lamellar structures and vesicles (also called polymeric liposomes); and (c) in the possibility of degradation of the polymer itself and of the self-assembled structures by oxidative reactions of the hydrophobic blocks. These features allow the preparation of carriers for bioactive lipo- or water-soluble materials having the benefits of incorporation into such structures, including enhanced cellular targeting because of the presence of antibodies or adhesion peptides on the surface. The polymers of the invention can also be prepared to contain hydrolytically or proteolytically unstable linkages that are used to trigger the release of the bioactive agents.

The polymers of the invention may be formed in the presence of sensitive biological materials, because of the high self-selectivity of the Michael addition reaction. Thus, one may couple at least one preformed block to the rest of the macromolecular material, permitting the possibility of incorporation of a biological molecule as one component of the materials.

In a first aspect, the invention features a method for the preparation of multiblock copolymers, involving generating and purifying a polymeric thiol precursor; producing a polymeric thiol from the polymeric thiol precursor; and using the polymeric thiol without isolation for episulfide ring-opening polymerization.

In a second aspect, the invention features a method for the preparation of multiblock copolymers, involving generating and purifying a polymeric thiol precursor; producing a polymeric thiol from the polymeric thiol precursor; and using the polymeric thiol without isolation for episulfide ring-opening polymerization; and exploiting the polysulfide terminal thiol for linking a preformed end-capping agent or for participation in a second polymerization step. In one embodiment of the above aspects of the invention, the multiblock copolymer consists of both hydrophilic and hydrophobic blocks. In another embodiment, the thiol precursor is a thioester, a dithioester, a thiocarbamate, a dithiocarbamate, a thiocarbonate, a xanthate, or a trithiocarbonate. Preferably the thiol precursor is also a polyether or a block copolymer where at least one of the blocks is a polyether, and where the thiol precursor is functionalized at one end with a thioester, a dithioester, a thiocarbamate, a dithiocarbamate, a thiocarbonate, a xanthate, or a trithiocarbonate. In another preferred embodiment, the thiol precursor is functionalized at the two ends if linear, or at every end if it is star-shaped or branched. In another embodiment, the thiol precursor includes a peptidic or saccharidic sequence.

In other embodiments of the above aspects of the invention, the episulfide has the following formula:

where R or R' is hydrogen, or an alkyl, hydroxyalkyl, alkoxyalkyl, phenyl, substituted phenyl, acyl, or carboxyalkyl group.

In a preferred embodiment of the second aspect of the invention, the end-capping agent is a polyether or a block copolymer where at least one of the blocks is a polyether, and it is functionalized with a Michael-acceptor group or with a good leaving group capable of nucleophilic substitution by a sulfur nucleophile. Preferably, the end-capping agent contains peptidic or saccharidic sequences or is a block copolymer containing aliphatic ester or anhydride groups and can undergo hydrolytical degradation.

In other embodiments of the above aspect of the invention the end-capping is given by the dimerization of the polymer itself, upon formation of disulfide bonds at the polysulfide terminal thiol.

In a third aspect, the invention features dispersions of the polymers of the above two aspects of the invention in water. In one embodiment, the dispersions contain self-assembled aggregates in the form of spherical micelles, worm-like or cylindrical micelles, or lamellar and other lyotropic structures.

In a fourth aspect, the invention features mono- or multilamellar vesicles including the polymers of the first two aspects of the invention in water.

In preferred embodiments, vesicles or micelles are contained within a pharmaceutically acceptable formulation. In another embodiment, the vesicles or micelles contain a drug and are contained within a pharmaceutically acceptable formulation. In yet another embodiment, the vesicles or micelles, in which the block copolymer contains at least one block consisting of polyethylene glycol, are contained within a pharmaceutically acceptable formulation. Preferably a targeting moiety is further immobilized on the surface of the vesicle contained within a pharmaceutically acceptable formulation.

In still another embodiment, the vesicles or micelles contain heparin or a heparin-binding moiety that is further immobilized on the surface of the vesicle or micelle contained within a pharmaceutically acceptable formulation.

In yet another embodiment, the vesicles or micelles contain a growth factor that binds heparin that is further immobilized on the surface of said vesicle contained within a pharmaceutically acceptable formulation.

In a preferred embodiment of the third and fourth aspects, the absolute and relative sizes of the hydrophilic and hydrophobic blocks are experimentally optimized to yield vesicles or micelles that escape recognition by the body's mechanisms of vascular particle clearance, such as recognition in the reticuloendothelial system.

In another preferred embodiment of the third and fourth aspects, the multiblock copolymer is responsive to pH, such that micelles or vesicles that are stable at pH 7.4 become destabilized at lower pHs, including the pHs encountered during endosomal and lysosomal trafficking.

In a fifth aspect, the invention features a protective environment within a self-assembled aggregate that is provided to a drug incorporated therein. For example, many drugs have been abandoned because of poor stability, such as antisense oligonucleotides, which, if made using normal DNA and RNA sequences and not chemical analogs or derivatives, demonstrate poor stability to DNA- and RNA-degrading enzymes. These analogs or derivatives generally display poorer binding to their intracellular targets. However, since the micelle or vesicle serves to protect the drug within the self-assembled aggregate, less stable drugs, such as normal DNA and normal RNA sequences, can be employed, rather than the less effective but more stable analog or derivative. This effect is the case with a number of drug forms.

In a sixth aspect, the invention features other excipients incorporated within a self-assembled aggregate, for example along with a drug to enhance the function of that drug. Such excipients can be membrane permeabilizing agents, to assist in transport of the incorporated drug across the membranes of the cell. Since the physics of the hydrophobic lamellae formed from the hydrophobic block are very different from the physics of the natural phospholipid membranes of the cell, agents may be incorporated that will render the cell membrane less stable or more permeable while not adversely affecting the stability or permeability of the micelle or vesicle. This ability to alter the permeability or stability of a membrane is useful, for example, in delivering drugs to the cytoplasm and nucleus, where the self-assembled aggregate can be designed to become less stable as it enters the endosome or lysosome and thus release the incorporated excipients, which then favorably affect the permeability of the endosomal or lysosomal membrane. Other excipients can be included as well, for example drug stabilizers.

In a seventh aspect, the invention features the oxidative degradation mechanism and products of the polymers of the first two aspects of the invention.

By a "thiol precursor" is meant any compound able to generate thiols as initiators for the in situ polymerization of episulfides. The thiol precursor may be thioesters, dithioesters, xanthates, dithiocarbamides, trithiocarbonates, or any compound, which, by nucleophilic attack, undergoes transesterification or transamidation reaction; a free thiol is generated and then deprotonated by a base, which can be the nucleophile itself or a non-nucleophilic compound, such as a tertiary amine (FIG. 1). All the thiol precursors are produced by attack of a sulphur-based nucleophile (e.g., sodium or potassium thioacetate, alkyl xanthate) on activated hydrophilic blocks.

By "ring-opening anionic polymerization of cyclic sulfides" is meant a process that occurs as follows. The attack of a nucleophile on a strained cyclic structure containing at least one sulfur atom, and the successive opening of the ring is referred to as ring-opening of a cyclic sulfide. If a chain reaction takes place, where every cyclic sulfide generates a thiolate that is a suitable nucleophile for another reaction, this is referred to as ring-opening polymerization of a cyclic sulfide (FIG. 2). Three-member, but sometimes also four-member rings, can be used. Mixtures of different cyclic sulfides can also be used, adding them sequentially (block copolysulfide) or directly in mixture (random copolysulfide).

Thiolates initiate this ring-opening polymerization much more effectively than alcoholates or amines and react much faster: in the case where an oxygen- or nitrogen-based initiator is used, competition between these and the growing chain thiolate end will occur, causing lower yield in the initiation step, higher molecular weight and broader molecular weight dispersity in the polymer.

By "Michael-type reaction" is meant the 1,4 addition reaction of a nucleophile on a conjugate unsaturated system (FIG. 3). Lewis acids or appropriately designed hydrogen bonding species can act as catalysts. The term "conjugation" refers in this case to the alternation of carbon-carbon, carbon-heteroatom or heteroatom-heteroatom multiple bonds with single bonds, and not to the linking of a functional group to a macromolecule, such as a synthetic polymer or a protein. Double bonds spaced by a CH or $CH_2$ unit are referred to as "homoconjugated double bonds."

Michael-type addition to unsaturated groups can take place in good to quantitative yields at room temperature and in mild conditions with a wide variety of nucleophiles. Unsaturated groups, such as vinyl sulfones or acrylamides, have been used to link PEG or polysaccharides to proteins through Michael-type reactions with amino- or mercapto-groups; acrylates and many other unsaturated groups have been reacted with thiols to produce cross-linked materials for a variety of biological applications.

The possibility of incorporating peptide or proteinaceous material is envisaged mainly in order to obtain a proteolytically degradable material or for specific recognition processes within it, but primarily by reaction with intentionally incorporated cysteine residues; pure protein PEGylation is outside of the scope of this invention.

Sulfur nucleophiles can be used in the Michael-type reaction: in the case of one pot reactions, the thiolate end of the polymer will react directly with the electrophile. As electrophiles, one can use hydrophilic blocks functionalized with reactive unsaturated groups, such as acrylates, itaconates, acrylamides, itaconamides, maleimides, vinyl sulfones, quinones, multisubstituted quinones, fused quinones (naphthoquinone and derivatives), vinyl pyridines and vinyl pyridinium ions and more generally, any unsaturation conjugated with electron withdrawing groups. Further examples of Michael-type reactions are given in Hubbell (U.S. application Ser. No. 09/496,231) and Hubbell et al. (U.S. application Ser. No. 09/586,937).

By "Nucleophilic substitution reaction" is meant the substitution reaction of a nucleophile on an electrophile bearing a good leaving group. The nucleophilic reaction uses the thiolate end of the polymer as nucleophile. As electrophiles, one can use hydrophilic blocks or low molecular weight compounds functionalized with good leaving groups, such as chlorides, bromides, iodides, tosylates, mesylates, triflates and more generally, every group that after nucleophilic substitution can generate a stable and non-reactive anion.

The AB polymer can be isolated, if a low molecular weight end-capping agent is reacted with the thiolate end of the polysulfide chain; in this way, one can produce and isolate a material that, in appropriate conditions, still exhibits a Michael-type reactivity. As an example, the end-capping agent can be a cyclic sulfone (three-member or four-member ring), which is converted to a sulfinic acid by nucleophilic attack. Sulfinic acid can further be used to react with quinone-containing species (FIG. 4). P is intended as a polymer structure containing the hydrophilic block (A, A' or C).

By "hydrophilic block" is meant hydrophilic polymers, for example, poly(ethylene glycol), poly(ethylene oxide)-co-poly(propylene oxide) di- or multiblock copolymers, poly(ethylene oxide), poly(vinyl alcohol), poly(ethylene-co-vinyl alcohol), poly(vinyl pyrrolidone), poly(acrylic acid), poly(ethyloxazoline), poly(alkylacrylates), poly(acrylamide), poly(N-alkylacrylamides), polypeptide, or polysaccharide, or poly(N,N-dialkylacrylamides), potentially bearing polar, ionic, or ionizable groups in the aliphatic chains This is not an exhaustive list, and other hydrophilic polymers can also be used. Low molecular weight compounds with sufficient hydrophilicity can be used as well.

All the hydrophilic blocks used for the initiation of episulfides ring opening polymerization must bear groups that can be converted to thiol precursors; for example, hydroxy groups can be transformed into sylate, mesylate, triflate, or other active esters and treated with a sulphur-based nucleophile; or can be converted to allyl derivatives and then added to a thioacid through a free radical addition (FIG. 5). In the present invention, the in situ generation of thiols on hydrophilic blocks is provided.

By "hydrophilic/lipophilic balance" (HLB) is meant an arbitrary scale from 0 to 40 depicting the amphiphilicity of a surfactant. Products with low HLB are more oil soluble. High HLB represents good water solubility. Generally HLB is a numerically calculated number based on the surfactants molecular structure and not a measured parameter.

By "adhesion peptides" is meant a peptide that binds to an adhesion-promoting receptor. It is straightforward to incorporate a variety of adhesion-promoting peptides that bind to adhesion-promoting receptors on the surfaces of cells, such as the RGD sequence from fibronectin or the YIGSR sequence from laminin. This can be done, for example, simply by mixing a cysteine-containing peptide with PEG diacrylate. During this step, the adhesion-promoting peptide becomes incorporated into one end of the PEG diacrylate; after purification of the product, the other end then reacts with a thiol-terminated polymer chain. In this case the adhesion site is pendantly incorporated into the material. One can also incorporate the adhesion site directly into the spine of the material. For example, one can synthesize the adhesion peptide (e.g., using solution phase chemistry) directly onto a polymer, such as PEG, and include at least one thiol (e.g., cysteine) per chain end and perform the same operation described above. Alternatively, one can include two or more thiols (e.g., cysteine) in the adhesion peptide or protein and let one react with PEG acrylate and the second initiate the episulfides polymerization. Alternatively, one can attach an adhesion peptide to the surface of a preformed self-assembled aggregate, such as the surface of a preformed micelle or vesicle. For example, the copolymer can be end-capped with a Michael acceptor, such as those groups described above. This end-capping can be readily accomplished by reacting the thiol-containing AB block copolymer with an excess of a PEG diacrylate to yield an ABA' copolymer that is terminally functionalized with an acrylate group. Micelles or vesicles can be formed from this material. A peptide containing a free cysteine can be dissolved in a suspension of these micelles or vesicles and the pH adjusted to a range where a Michael-type addition between the self-assembled aggregate-bound acrylate reacts with the free thiol on the adhesion peptide.

By "proteolytically degradable" is meant containing a substrate for plasmin, elastase, or matrix metalloproteinases (MMPs), such as collagenase, that can be introduced in the hydrophilic block main chain; the degradation characteristics of the polymer and of the carrier can be manipulated by changing the details of the peptide. One may make a material that is degradable by collagenase, but not plasmin, or by plasmin, but not collagenase. Furthermore, it is possible to make the material degrade faster or slower in response to such an enzyme, simply by changing the amino acid sequence so as to alter the $K_m$ and $k_{cat}$ of the enzymatic reaction. The peptide degradation can influence the carrier behavior and the eventual release of active substances: if the protease site is incorporated in a way that its cleavage causes a big change in the hydrophilic/lipophilic balance of the amphiphilic polymer, proteolysis will determine structural changes in the carrier, e.g., liposome collapse, and so boost the release. Alternatively, the protease site could be directly linked to the pharmacologically active group; enzymatic hydrolysis will directly free it.

By "targeting moiety" is meant any biological recognition ligand attached to the self-assembled aggregate, such as a micelle or vesicle, that enhances binding of the aggregate at a particular site in the body. Targeting moieties include a growth-factor receptor-binding moiety, a cell-surface receptor-binding moiety, a DNA-binding moiety, an RNA-binding moiety, adhesion peptides, adhesion-promoting branched saccharides, such as the sialyl Lewis X and related structures of selectin binding, combinatorially-discovered peptides, peptidomimetics, saccharides, saccharides and peptides that bind to an adhesion-promoting receptor, organic ligands, growth factors, growth factor binding sites, antibodies, antibody fragments, single chain antibodies, DNA and RNA sequences, nuclear localization sequences, pathogen mimetics, heparin and proteoglycan-binding peptides and ligands, for example. Further examples of targeting moieties are given in Hubbell (U.S. application Ser. No. 09/496,231) and Hubbell et al. (U.S. application Ser. No. 09/586,937).

By "growth factor binding sites" is meant heparin-binding peptides employed to bind heparin that are, in turn, employed to bind heparin-binding growth factors, such as aFGF, bFGF, VEGF, BMP or TGF. As such, if the heparin-binding growth factor and heparin are mixed with the block copolymer functionalized with heparin-binding peptide (for example, as described in the adhesion sites section), the resulting material will slowly release the growth factor; if the peptide presents a proteolytically cleavable sequence, the carrier will hold most of it until an enzymatic event releases the growth factor by degradation of the polymer chain. This enzymatic release is one of the natural functions of the extracellular matrix in vivo, to serve as a depot for growth factors which become released in injury by local cellular activity. Another related way to sequester heparin binding growth factors is more directly through the use of covalently incorporated heparin mimics, e.g., peptides with negatively charged side chains that directly bind growth factors. Growth factors bound to self-assembled aggregates such as micelles and vesicles may be useful as targeting moieties.

Other features and advantages will be apparent from the following detailed description and from the claims.

BRIEF DESCRIPTION OF THE DRAWINGS

FIG. 8 is a crossed polarized light optical microscopy image (10× magnification) of a 50% wt. mixture of a triblock copolymer made of propylene sulfide and ethylene glycol and water.

FIG. 13 is a schematic representation of examples of pH-sensitive vesicles; the black spheres represent groups, e.g. imidazoles, which after protonation increase their hydrodynamic volume and their charge, giving rise to self-repulsion forces and to higher osmotic pressure. The final aggregates are supposed to show a micellar structure, but also bigger colloidal particles or other aggregates can be formed.

DETAILED DESCRIPTION OF THE INVENTION

Figure 1:
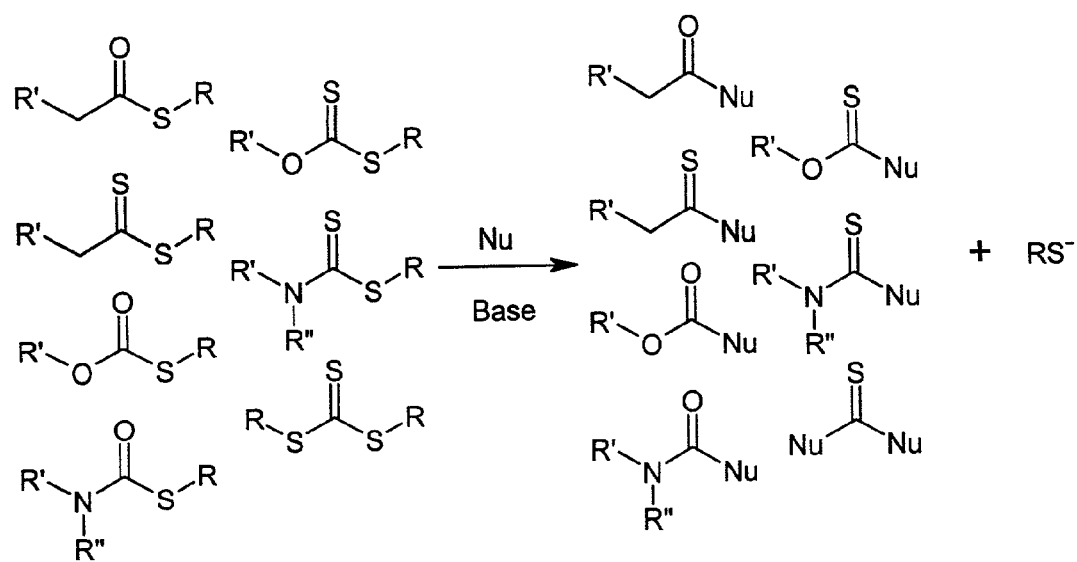
FIG. 1 is a schematic representation of thiol precursors. In this figure, R' and R"=H, alkyl, R=hydrophilic block, Nu=primary or secondary amine, or alcoholate, and Base=a primary, secondary, or tertiary amine, or alcoholate, or inorganic bases.
Figure 2:
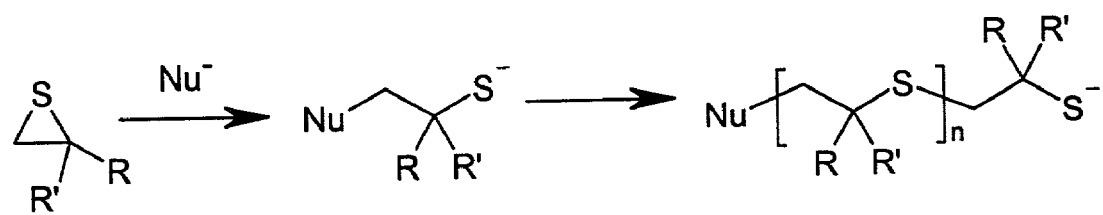
FIG. 2 is a schematic representation of an example of ring-opening anionic polymerization of cyclic sulfides. In this figure, R, R', R"=H, alkyl, hydroxyalkyl, alkoxyalkyl, phenyl, substituted phenyl, acyl, or carboxyalky.
Figure 3:
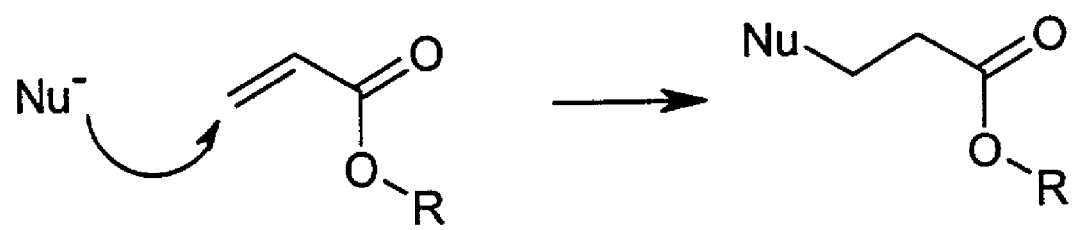
FIG. 3 is a schematic representation of a Michael-type reaction.
Figure 4:
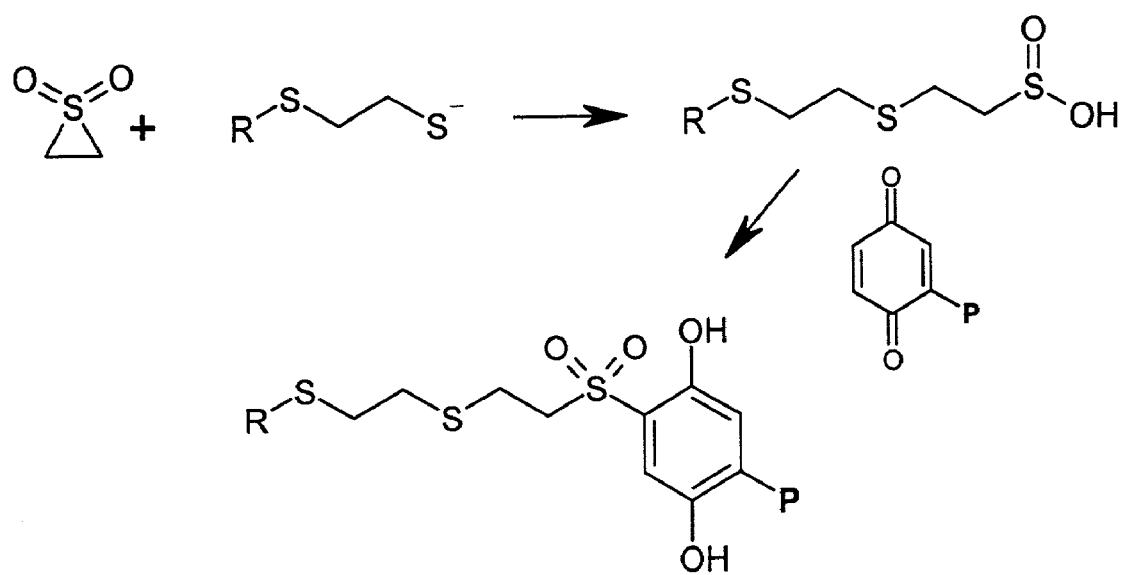
FIG. 4 is a schematic representation of how an AB polymer can be isolated if an end-capping agent is reacted with thiolate end of the polysulfide chain. In this way, one can produce and isolate a material that, in appropriate conditions, still exhibits a Michael-type reactivity.
Figure 5:
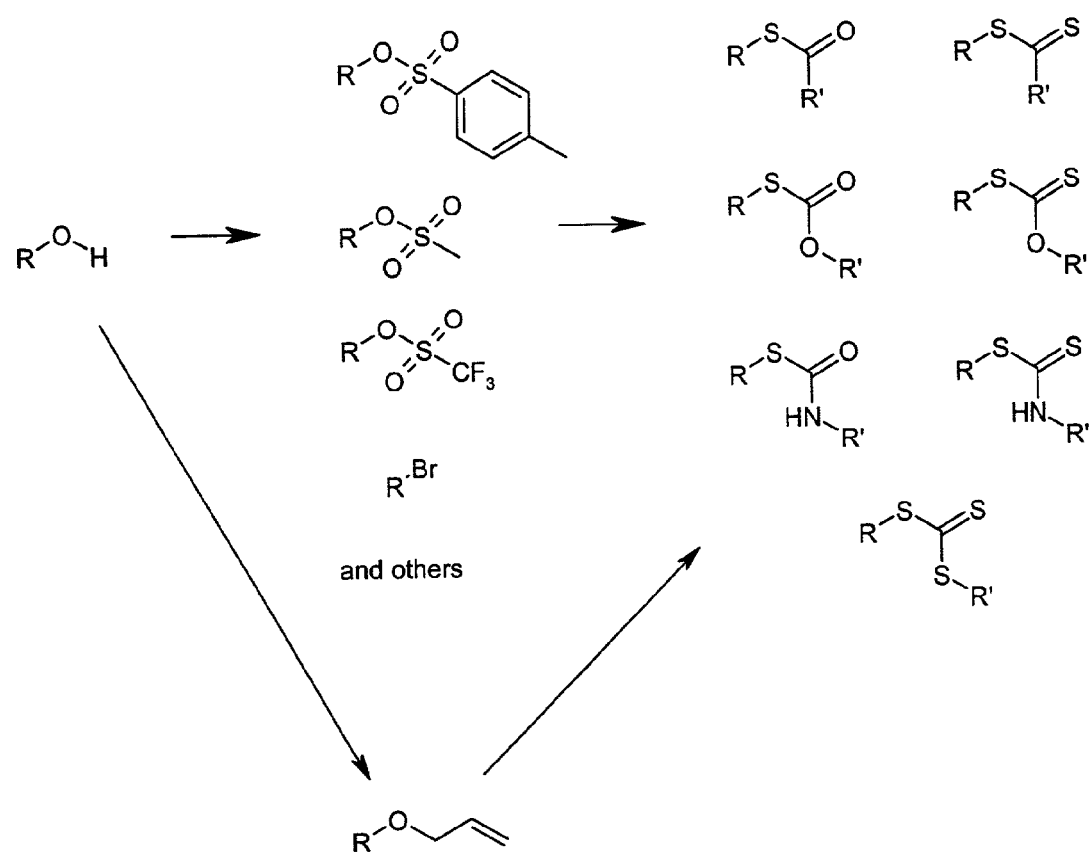
FIG. 5 is a schematic representation of groups on hydrophilic blocks that may be used for the initiation of episulfides ring opening polymerization.

The Chemical Reactions Used for Block Copolymer Synthesis

A novel scheme for the one-pot (single vessel) synthesis of block copolymers has been developed; hereafter the preparation method of symmetric (ABA or AB-S-S-BA) or asymmetric (ABC, or ABA' if the third block is physically, but not chemically different) block copolymers is described. These copolymers can contain reactive groups in one or both hydrophilic groups and in the last case, the two reactive groups can be of different nature (designated * and #), to yield for example ABA*, #ABA*, *AB-S-S-BA*, ABC*, or #ABC*. The possibility to form complex block structures, the tolerance to a variety of functional groups (due to the presence of thiolates as propagating species), the exploitation of the thiolate end for Michael-type addition, nucleophilic substitution and disulfide bond reactivity, and the use of a thiol precursor differentiate the present polymerization scheme from the only literature report on the synthesis of block copolymers containing polysulfide and polyether blocks (Inoue et al., *Macromolecules* 1990, 23, 3887–3892 and 1991, 24, 3970–3972), which made use of thiolate-initiated photopolymerization of epoxides for yielding BA copolymers.

Structure of the A Block:

Polyethylene glycol (PEG) provides a very convenient building block for the hydrophilic parts (A, A', C), but also other polymers can be used, such as end-functionalized poly(N-vinyl pyrrolidone) (PNVP), poly(acrylamide) (PAM), poly(N-alkyl or N,N-dialkylacrylamides), and poly(acrylates) containing hydrophilic and ionizable groups (a more comprehensive description follows).

Peptidic sequences can be contained in one of the hydrophilic blocks, or indeed can be of one of the hydrophilic blocks, and can be used to modify the functionality and the behavior of the self-assembled carriers; for example, proteolytically degradable sequences can influence the carrier stability in the presence of enzymes, with an enzymatically triggered release of a carried drug.

Structure of the B block:

Poly(alkylene sulfides) provide a convenient building block for the B block, because of their high hydrophobicity and low glass transition temperature relative to the working temperature. A low value of glass transition temperature is necessary for the mobility and membrane-forming ability of the polymer chains; preferred values are those below −20° C. Propylene sulfide, cyclohexene sulfide, and any other episulfide derived from terminal or internal double bonds can be used for the preparation of homopolymeric or block- or random-copolymeric hydrophobic blocks. Amorphous block or random copolymers of ethylene sulfide can also be used; in a preferred formulation the average length of ethylene sulfide sequences does not exceed ten repeating units.

Structure of the End-Capping Groups:

Michael-type acceptors provide a very convenient structure for end-capping reactions in mild conditions; hydrophilic polymers or oligomers end-functionalized with a Michael-acceptor group can be used. Homopolymers, random, and block copolymers of the compounds mentioned in the definition of hydrophilic blocks can be used. In a preferred formulation, a polyether with molecular weight greater than 300 is used, bearing an electron-poor double bond as a terminal group. In another formulation, the hydrophilic polymer or oligomer is end-functionalized with a group that can undergo nucleophilic substitution reactions with thiolate anions, such as iodo- or bromo acetates or acetamides, substituted or non-substituted benzyl bromides or iodides and others. The list is not intended to be exhaustive. In a preferred formulation, the polymeric or oligomeric end-capping agent bear also functionalities, such as peptidic or saccharidic structures for biological functionality, esters, anhydrides, Schiff bases or acetals for hydrolytical degradation. In another formulation, the end-capping agent is a low molecular weight compound bearing a Michael-acceptor or a substrate for nucleophilic subsitution reactions of the kind mentioned above. The low molecular weight compound can be only the substrate of Michael-type addition or nucleophilic substitution or bear other functionalities, such as peptidic structures for biological functionality, esters, anhydrides, Schiff bases or acetals for hydrolytical degradation.

Relative Structure of the A and B Blocks:

Varying the weight fraction of the hydrophobic block B provides an easy way to control the formation of lyotropic mesophases. When the length of the B block in ABA or AB architecture is much lower than the length of hydrophilic A blocks, then micelles are preferentially formed in a wide range of concentrations. The Critical Micelle Concentration (CMC) is therefore shifted to higher values when compared to ABA copolymers having longer B blocks.

In a preferred formulation at a concentration of 1% wt. in water, a triblock copolymer containing a weight fraction of 0.5 of B block forms a lamellar or vesicular aggregate. In another formulation at a concentration of 1% wt. in water, a triblock copolymer containing a weight fraction of 0.1 of B block will form a micellar lyotropic aggregate. At a constant weight fraction of hydrophobic block, the length of A and of the end-capping group can influence the stability of the lyotropic aggregate; long hydrophilic chains can for example stabilize vesicular aggregates against micellar ones.

Relative Structure of the A, B and End-Capping Groups:

Groups that can undergo ionization or hydrolysis reactions can be present in A, B and in the end-capping group; their chemical transformation provides a convenient way to change the hydrophilic/lipophilic balance of the molecule and therefore to trigger the destabilization of the aggregates. In a preferred formulation at the junction between A and B or between B and the end-capping group or at both junctions are present groups capable of protonation at pH<7.3, such as imidazole (e.g. in hystidine residues of a peptidic structure), or deprotonation at pH>7.5, such as phenols (e.g. in a tyrosine residues of a peptidic strucure). Upon exposure to water solution at pH<7.3 or >7.5, respectively, the ionization of the residues mentioned above will increase the free energy of the A/B interface causing a rearrangement, for example from a vesicular to a micellar structure, and at the same time the release of any encapsulated molecule. In another formulation, hydrolizable groups are presented at the A/B junction; anhydrides, esters, acetals, Schiff bases can provide convenient hydrolizable structures, but other groups can also be used. Upon hydrolysis, the A group will be cleaved, destabilizing the aggregate and causing the release of encapsulated molecules in the manner described above. In another preferred formulation, the groups that can undergo protonation or deprotonation or hydrolysis reactions are present in the B block; the polymerization of episulfide monomers containing the above mentioned groups provides a convenient method for the incorporation of these structures in the B block, but also functionalization of the preformed polymers can be used. Upon reaction the hydrophobicity of the B block will be decreased and a rearrangement will take place with the release of the encapsulated molecules in the manner described above. In another formulation, the groups that can undergo protonation or deprotonation or hydrolysis reactions are present at the end of the A block or at the end of end-capping group or at the end of both. Upon reaction the hydrophilicity of the A block or of the end-capping group will be increased, and this increase will cause an expansion of the molecular coil. In a preferred formulation the reactive groups will be present in a sequence; the expansion of the molecular coil will be a function of the number of groups in the sequence and will increase with this number, because of increased electrostatic repulsion and local osmotic pressure after the reaction. The expansion of the coil will determine a rearrangement of the structure of the aggregate, with release of the encapsulated molecules in the manner described above.

Initiation:

In general, the block A is terminated with a group that can be converted to a thiol via nucleophilic attack; the thiol is in most cases generated as thiolate and not isolated, but immediately used.

The great advantage of this technique is that the precursor can be isolated, purified, and stored without disulfide bond formation. In thiol-initiated polymerizations, the presence of disulfides often makes a precise estimation of the required initiator concentration impossible. In the present invention, the precursors are thioesters and similar compounds that are not subject to oxidative coupling (a more detailed description follows below).

Polymerization Techniques:

Several different polymerization techniques can be used, employing thiols as initiators or chain transfer agents: e.g., ring-opening polymerization of cyclic sulfides (three-member rings, hereafter called episulfides), free radical polymerization, or Michael-type polyaddition. The polymerization technique will determine the chemical structure of the hydrophobic block (B); examples of the application of different polymerization techniques are listed hereafter:

A) The result of the living anionic episulfides ring-opening polymerization is a thiolate-terminated, potentially reactive diblock copolymer AB; this group can be used for the introduction of a third block by using a Michael-type addition reaction on an A' or C block terminated with an electron-poor olefin, such as an acrylate, a quinone, a maleimide, a vinyl sulfone, or other electron-poor olefins. The chemical reaction system of use in this invention exploits Michael-type addition reactions, in which one component, the terminus of the B block, possesses a strong nucleophile and the other component, the terminus of the C block with which reaction will be carried out to couple it to the terminus of the B block, possesses an unsaturation.

These reactions are very fast and self-selective, and a variety of functional groups on the C or A' structure can be tolerated.

A variation to the procedure presented above is the use of a reagent to end-cap the polysulfide chain; this end-capping allows for the isolation of the diblock copolymer without disulfide bonding formation; the Michael-type reactivity can be obtained in a second stage with an appropriate chemical treatment.

If thiols can be generated in a number higher than one in the A block, multiblock copolymers are obtained; if the functionality of A is two, a linear pentablock (CBABC or A'BABA') is obtained; if the functionality of A is more than two, the resulting polymer has a star shape and the number of thiols determines the number of arms of the star.

B) The in situ generation of thiols can be used also for Michael-type polyaddition, without making use of episulfides; using C blocks terminated with Michael-acceptor groups, block copolymers with AC (with A and C each having one reactive group), ACA (with A having one, and C two), CAC (with A having two, and C one) and (AC)n (with A and C each having two) structures can be produced.

C) If thiols are generated in the protonated form, they can be used as chain transfer agents for a radical polymerization: a monomer or a monomer mixture can be added after the thiol preparation, together with an initiator. Thermally or photochemically-initiated radical polymerization can be used: in the first case, the initiator is an azo or peroxide-containing compounds, such as AIBN or benzoyl peroxide; in the second case, it is a photosensitizer, such as benzophenone, or a mixture of a sensitizer and an initiator, such as riboflavin or Eosin and triethanolamine.

With such a polymerization technique, a mixture of AB and ABA structures will produced, with composition depending on the balance between coupling and disproportionation of the polymeric radicals, but generally with AB as the major component.

D) Finally, it is possible to prepare the AB polymer and oxidize in situ simply by exposure to air, converting the thiolate end group to disulfide and generating an ABBA polymer; this reaction can be accelerated by the presence of metal ions, such as iron or copper, even in traces. This polymer can be degraded to the original AB structure under reducing conditions.

Functional Groups:

The use of episulfide polymerization for the synthesis of the hydrophobic block makes possible the hydrophilic thiol precursor (#A) to bear every functional group not sensitive to thiolates or to bases, used for the deprotection of the thiol precursor. For example, amides, alcohols, ethers, nitrites, olefins, aromatic groups, Schiff bases, acetals, most saccharidic, and steroidal structures.

The use of Michael-type addition or nucleophilic substitution as end-capping reactions makes possible the end-capping agent (A*) to bear every functional group not sensitive to thiolates. For example, alcohols, carboxylates, esters, amides, ethers, nitrites, anhydrides, Schiff bases, acetals, most peptidic structures (provided the absence of unprotected cysteines and the previous deprotection of any acid residues), most saccharidic, and steroidal structures.

The Degradation Steps

Figure 6:
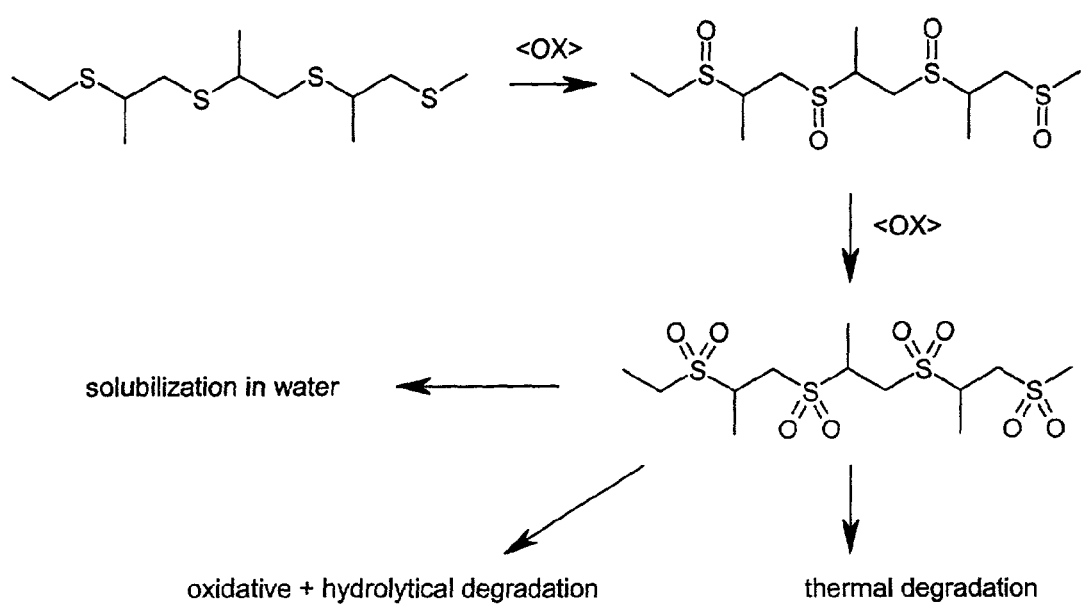
FIG. 6 is a schematic representation of the degradation of the self-assembled carriers of the present invention.

In order to avoid irreversible accumulation in the targeted organs, the self-assembled carriers should demonstrate some form of degradation. Polysulfides are known to readily undergo oxidation to polysulfoxides and even to polysulfones (FIG. 6), e.g., by the action of mild oxidizing agents, such as hydrogen peroxide. Under biological conditions, this oxidation can be performed extracellularly, e.g., by macrophages, or intracellularly after cellular uptake into an endosomal or lysosomal compartment. A similar kind of reaction is used for oxidizing thioether-terminated PEGs (used as emulsifiers in pulp and paper processing) in order to break wastewater foams (Wood et al., U.S. Pat. No. 4,618,400), but it has not been used in degradation in medical materials under physiological conditions.

The conversion of the polysulfides to polysulfoxides can solubilize the amphiphilic polymers in water, allowing elimination through excretion. The conversion can trigger the instability of self-assembled aggregates, e.g. the conversion of gels to micelles or soluble polymers, the conversion of vesicles to micelles or soluble polymers, or the conversion of micelles into micelles of different size and shape or to soluble polymers. Destabilizing the aggregate can also trigger the release of encapsulated compounds, e.g., a drug. In this sense, the word 'degradation' refers more to the size and structure to be eliminated from the body or the body's ability to eliminate it than the molecular weight of the polymer itself. As such, this oxidative 'degradation' represents a new method of biomaterials clearance from the body, especially in drug delivery applications. Redox mechanisms can, however, also be used to affect more dramatically the molecular weight of the polymer. This effect is true, for example, with the AB-S-S-BA copolymers, which roughly halve in molecular weight during reduction. The oxidation to sulfones can increase the water solubility and at the same time the depolymerization and other hydrolytical chemical degradation. The mechanisms of clearance of soluble polymers are relatively well understood. The most important such mechanism is clearance via renal filtration, the effective molecular weight cutoff of which is approximately 30,000. Particles of size less than approximately 100 nm can be cleared from the bloodstream in the liver. Lymphatic uptake also plays an important role.

Self-Assembling of the Carrier

Amphiphilic block copolymers have long been used as surfactants and dispersants in a wide variety of applications; the formation of organized structures in a solvent that is selective for one of the blocks is at the basis of this behavior.

Well-defined self-assembled structures, such as spherical or cylindrical micelles, lamellae, or vesicles (Booth et al., *Macromol. Chem., Rapid Commun.* 2000, 21, 501–527; Won, *Science* 1999, 283, 960–963; Discher et al., *Science* 1999, 284, 1143–1146; and Eisenberg et al., *Macromolecules* 1998, 31, 3509) have been observed in poly(oxyalkylene) block copolymers. The concentration of the polymer solution and the temperature greatly influence the kind of aggregates that can be formed: changing, e.g., from liquid spherical micellar phases to cubic phases of spherical micelles and finally to hexagonal phases of cylindrical micelles upon an increase in temperature (Mortensen, *Progr. Coll. Polym. Sci.* 1993, 93). The phase diagram and accessible structures of the amphiphilic block copolymers exhibit a dependence on the block length and number, i.e. basically, on the hydrophilic/lipophilic balance.

Block copolymers of PEG with poly(ethylethylene) have shown a propensity to form worm-like micelles like formation at a ratio 55/45 between hydrophilic and hydrophobic repeating units (total MW=4900), and to form lamellar structures at a ratio 40:37 (total MW=3900).

In suitable conditions for the generation of micelles, the self-assembled carrier can be used for the encapsulation of hydrophobic drugs. When lamellar phases are to be formed, vesicles can be generated from the lamellar structure bending; in this way, water-dissolved drugs can be entrapped in the internal cavity of the vesicle.

This invention describes materials capable of generating a wide variety of structures; for example, a material containing long sequences of hydrophilic groups is able to form micelles, while a high hydrophobic content facilitates the formation of lamellar gels, and, under suitable conditions, vesicles.

The formation of vesicles can also be achieved by adding to water a solution or colloidal suspension of the copolymer in an organic solvent and subsequently removing the organic solvent.

Through this invention, we also describe the preparation of block copolymers having a triblock structure, among others, of the form ABA', where A and A' differ only in the molecular weight. In this case, when polymeric vesicles are formed, a preferential localization of the bigger residue on the outer side of the vesicle can take place under some conditions. In this way, the functionalization with bioactive groups can be directed selectively towards the internal or the external side of the vesicle, depending on which hydrophilic residue has been derivatized. Even in the absence of such preferential localization, presentation of ample amounts of a targeting ligand or other biological moiety can readily be achieved.

Biomedical Applications for Self-Assembled Carriers

Colloidal particles such as nanospheres, liposomes and micelles have been studied extensively for site-specific drug delivery. Unless this is a target, the particles must escape capture by the reticuloendothelial system (RES) of the liver and the great filtration activity of the lungs. In recent years prolonged survival of colloidal systems in the blood has been obtained by the use of PEG-containing amhiphiles (Lasic et al., Ed. *Stealth Liposomes*; CRC Press: Boca Raton, Fla., 1995); thanks to the marked reduction of opsonization by plasma proteins, the macrophages clearance of PEG-based liposomes has been drastically reduced (Torchilin et al., *Biochim Biophys Acta* 1994, 1195, 11–20).

A variety of ligands, such as antibodies, growth factors, cytokines, adhesion factors, oligonucleotide sequences and nuclear localization sequences has served to enhance the delivery capabilities of PEG-coated liposomes, and it has been demonstrated that the maximal activity is shown by ligands tethered to the distal end of PEG chains (Blume et al., *Biochim. Biophys. Acta* 1993, 1149, 180–184; Zalipsky et al., *Bioconjugate Chem.* 1995, 6, 705–708; Zalipsky, *J. Controlled Release* 1996, 39, 153–161; Gabizon, *Bioconjugate Chem.* 1999, 10, 289–298). Some ligands can lead to very efficient cellular uptake, such as the use of growth factors, for example, fibroblast growth factor to effect cellular uptake of DNA formulations. Other ligands can lead to very efficient intracellular trafficking, such as nuclear localization sequences, which is particularly useful in applications such as nonviral gene delivery.

The polymers of the present invention are useful for any application in the controlled release of a drug, where a self-assembled carrier can be used. The advantages in using the block copolymers described herein are:

(i) the flexibility of the structure: with the same process and with the same family of reagents, a variety of structures can be generated (e.g., just by varying the amount of monomeric episulfide in the thiolate-initiated polymerization, one can obtain a different length of the hydrophobic block and a different behavior in water);

(ii) the ease of insertion of targeting moieties (also referred to as targeting groups) that enhance the selectivity of the drug delivery;

(iii) the possibility of targeted proteolytic degradation, by insertion of specific peptide sequences, or oxidative degradation, through slow oxidation or cellularly induced oxidation during cellular uptake;

(iv) the amount of PEG that can be displayed upon the surface of the self-assembled system, in which essentially every component molecule within the system contains a grafted PEG or other opsonization-preventing hydrophilic polymer;

(v) the possibility of protecting otherwise sensitive drugs within the protective environment of a self-assembled aggregate such as a micelle or vesicle, to protect the drug from degradation or clearance prior to reaching its intended target;

(vi) the possibility of triggering the release of the contents, e.g., a drug, of the self-assembled aggregate, such as a micelle or vesicle, through sensitivity of the aggregate to the environment, such as triggering a release based on the lowering of pH, increase in the extent of oxidation, and increase in the concentration of proteases during the process of intracellular trafficking from the endosome to the lysosome; and (vii) the possibility of incorporating excipients along with a drug to help it in reaching its final biological target, such as incorporation of agents that assist in destabilizing or permeabilizing biological membranes, such as the endosomal or lysosomal membranes, to enhance transport of the drug into the cytoplasm or ultimately into the nucleus.

The following examples are to illustrate the invention. They are not meant to limit the invention in any way.

EXAMPLE 1

Preparation of the Thiol Precursors

Preparation of PEG Thioacetate Route A:
Preparation of Monomethoxy-PEG Tosylate (MPEGOTs):

2 g ($2.7 \times 10^{-3}$ mol) of monomethoxy poly(ethylene glycol) (MW 750 D)—MPEG 750 (Fluka)—were introduced in a two-neck reaction flask under dry Ar atmosphere and dissolved in 30 mL of $CH_2Cl_2$.

2.2 mL of triethylamine (TEA) (0.016 mol) were added and, under vigorous stirring, 2.57 g (0.0135 moles) of p-toluene sulphonyl chloride were added to the mixture. The reaction mixture was left for 24 hours at room temperature and then filtered to remove salts formed during reaction (triethylammonium hydrochloride). The collected solution was concentrated at the rotary evaporator and filtered on a celite bed. The solution was then treated with neutral alumina, filtered on paper, and precipitated in cold ether.

Preparation of Monomethoxy-PEG Thioacetate:
2 g of MPEGOTs (MW ~900D, ~$2.22 \times 10^{-3}$ mol) were dissolved in 30 ml of acetone. 0.76 g of potassium thioacetate (~$6.67 \times 10^{-3}$ mol) was added to the reaction mixture and left under vigorous stirring overnight at room temperature.

Non-dissolved salts were eliminated by paper filtration. The solution was concentrated at the rotary evaporator, and PEG thioacetate was collected by precipitation in cold ether. The product was then dissolved in $CH_2Cl_2$, and the solution was extracted with water several times. The $CH_2Cl_2$ solution was dried with $Na_2SO_4$ and then precipitated in cold ether.

Preparation of PEG Thioacetate Route B:

Preparation of Allyl PEG:

2 g ($2.7 \times 10^{-3}$ mol) of monomethoxy poly(ethylene glycol) (MW 750 D)—MPEG 750 (Fluka)—are introduced in a two-neck reaction flask under dry Ar atmosphere and dissolved in 30 mL of $CH_2Cl_2$. 2.2 mL of triethylamine (TEA) (0.016 mol) are added, and under vigorous stirring, 1.63 g (0.0135 moles) of allyl bromide are added to the mixture. The reaction mixture is left for 24 hours at room temperature and then filtered to remove salts formed during reaction (triethylammonium hydrochloride).

The collected solution is next concentrated at the rotatory evaporator and filtered on a celite bed. The solution is then treated with neutral alumina, filtered on paper, and precipitated in cold ether.

Preparation of PEG Thioacetate:

2 g of allyl PEG (MW ~790D, ~$2.53 \times 10^{-3}$ mol) are dissolved in 30 mL of THF together with 0.4 g of thioacetic acid ($5.26 \times 10^{-3}$ mol) and 0.85 g of azo-bis-isobutirronitrile (AIBN). The solution is heated to 60° C. for 20 hours, then is concentrated at the rotary evaporator, and is precipitated in cold ether.

Preparation of O-Ethyl-S-Monomethoxy-PEG Xanthate:

2 g of MPEG-OTs (monomethoxyPEG, terminally activated with tosyl, MW ~900D, $2.22 \times 10^{-3}$ mol) were dissolved in 30 ml of NMP. 1.07 g of potassium O-ethyl xanthate (~$6.67 \times 10^{-3}$ mol) were added to the reaction mixture under vigorous stirring overnight at room temperature. The solution was concentrated at the rotary evaporator, dissolved in $CH_2Cl_2$, and then filtered with a paper filter. O-ethyl-S-monomethoxy-PEG xanthate was collected by precipitation in cold ether. The product was then dissolved in $CH_2Cl_2$, and the solution was extracted with water several times. The $CH_2Cl_2$ solution was dried with $Na_2SO_4$ and then precipitated in cold ether.

Preparation of Bis-MonomethoxyPEG Trithiocarbonate:

To a suspension of 10 g of potassium hydroxide (0.18 mol) and 11.5 g of carbon disulfide (0.16 mol) in 100 ml of THF are added 12.9 g of monomethoxy-monobromo PEG 750. The mixture is refluxed for 24 hours, and then the solid is filtered out, and the THF was evaporated. The crude product is dissolved in $CH_2Cl_2$, and the organic solution is then extracted with water, dried with $Na_2SO_4$, and precipitated in hexane.

Preparation of Thioacetate-Functionalized PVA:

Preparation of Partially Tosylated Poly(vinyl alcohol):

2 g of poly(vinyl alcohol) (MW 15,000, $4.5 \times 10^{-2}$ mol OH) are reacted with 5 g ($5.3 \times 10^{-2}$ mol) of tosyl chloride and 4.8 mL of TEA (0.063 mol), as described in the example for preparation of PEG thioacetate (Route A). The polymer solution is then precipitated in hexane.

Preparation of Partially Thioacetate-Functionalized PVA:

The polymer obtained above was reacted with potassium thioacetate as in the example for the preparation of PEG thioacetate (Route A). The polymer solution is them precipitated in hexane.

EXAMPLE 2

One-Step Preparation of Non-Functionalized and Functionalized Block Copolymers

Generation of Thiolate from PEG Thioacetate, Episulfide Polymerization and End Capping of the Polysulfide Chain with PEG Monoacrylate:

0.3 g of monomethoxy PEG 750 thioacetate were introduced into a two-neck flask under dry Ar atmosphere and dissolved in freshly distilled THF. One equivalent of MeONa in a 0.5M solution in MeOH was added and left at room temperature for 30 minutes.

The episulfide (propylene sulfide) was then added in an appropriate quantity (generally between 25 and 50 equivalents; the number of equivalents determines the molecular weight of the polysulfide block) under vigorous stirring. After approximately 30 minutes, the polymerization was complete, and 10 equivalents of PEG monoacrylate as end capping agent were introduced to react overnight at room temperature. The copolymer was collected by precipitation in MeOH.

Preparation of Peptide-End-Functionalized PEG Monoacrylate:

PEG diacrylate of molecular weight 8,000 (230 mg/mL) is allowed to dissolve in HEPES buffered saline (10 mmol HEPES (Sigma), 8 g/L NaCl, pH 7.4) for 1 hour. Triethanolamine (Aldrich, 15.3 µL/mL) is added, and the pH of the solution is adjusted to pH 8 with 6 N HCl. Cysteine containing peptides are dissolved in 5 mL of HEPES buffered saline and added to 40 mL of the PEG diacrylate solution with vortexing. The reagents are incubated for 6 hours. The solution is then dialyzed against pure water for 24 hours and freeze-dried. The polymer is dissolved in 5 mL of dichloromethane and precipitated in hexane.

Generation of Thiolate from PEG Thioacetate, Episulfide Polymerization, and End Capping of the Polysulfide Chain with Peptide-Terminated PEG Monoacrylate:

The same procedure as in the example for the generation of thiolate from PEG thioacetate, episulfide polymerization, and end capping of the polysulfide chain with PEG monoacrylate is performed but using the peptide-terminated PEG monoacrylate synthesized as in the example for the preparation of peptide-end-functionalized PEG monoacrylate, instead of PEG monoacrylate.

Generation of Thiolate from PEG Thioacetate, Episulfide Polymerization, and Oxidative Dimerization of the Terminal Thiol of the Polysulfide Chain:

The same procedure as in the example for the generation of thiolate from PEG thioacetate and episulfide polymerization was performed, but no end-capping agent was used. The solution was then exposed to air for 12 hours. The copolymer was collected by precipitation in MeOH.

EXAMPLE 3

Two Step Preparation of Block Copolymers

Generation of thiolate from PEG thioacetate, episulfide polymerization, and end capping of the polysulfide chain with thiirane dioxide was performed as in the example for the generation of thiolate from PEG thioacetate, episulfide polymerization, and end capping of the polysulfide chain with PEG monoacrylate, with thiirane dioxide used in the place of PEG monoacrylate.

EXAMPLE 4

Analysis of Polymeric Lamellar Structures

Optical Microscopic Analysis on Films

A triblock copolymer made of a sequence 16:25:8 of monomeric units of, respectively, ethylene glycol, propylene sulfide, and ethylene glycol, was dissolved in $CH_2Cl_2$, and the solvent was evaporated to obtain a polymer film. This film was hydrated with bidistilled water and a birefringence pattern immediately developed under optical microscopic observation with crossed-polarizers.

TEM Analysis

A triblock copolymer made of a sequence 16:25:8 of monomeric units of, respectively, ethylene glycol, propylene sulfide, and ethylene glycol, was dissolved in $CH_2Cl_2$, and the solvent was evaporated to obtain a polymer film. Water was added in order to produce a 50% w/w dispersion in the form of a gel that was homogenized by vortexing for five minutes.

Figure 9A:
FIGS. 9A, 9B, and 9C are pictures obtained by freeze fracture TEMs of vesicles formed from a triblock copolymer made of propylene sulfide and ethylene glycol.
Figure 9B:
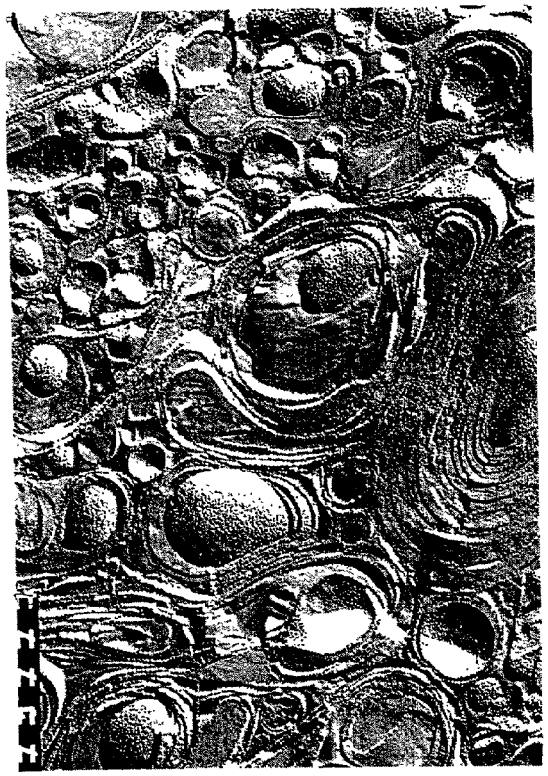

Additional water was added to reduce the dispersion to a concentration of 20% of the polymer w/w, and the sample was then freeze fractured utilizing the technique of ultra-rapid cooling with liquid propane (Gulik-Krzywicki et al., Langmuir 1996, 12, 4668–4671). TEM images were recorded on graphite replicas (FIGS. 9A and 9B).

EXAMPLE 5

Morphology

Figure 7A:
FIGS. 7A and 7B are TEMs of worm-like micellar structures of the present invention.
Figure 7B:
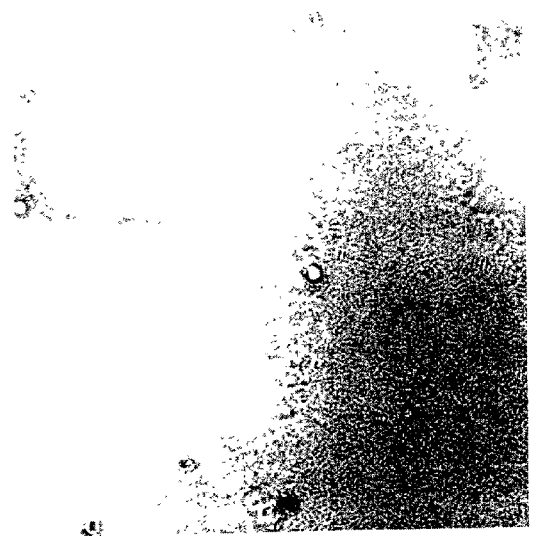

The multiblock copolymers prepared with the methods described herein self-assemble in water; for example, a polymer constituted by 25 monomeric units of propylene sulfide and 24 of ethylene glycol, in a sequence 16:25:8, was dispersed in water at a concentration of 0.1% w/w, then slowly dried; TEM investigation showed the formation of worm-like micellar structures (FIGS. 7A and 7B), with a certain tendency towards the formation of coiled higher order aggregates.

Figure 9C:
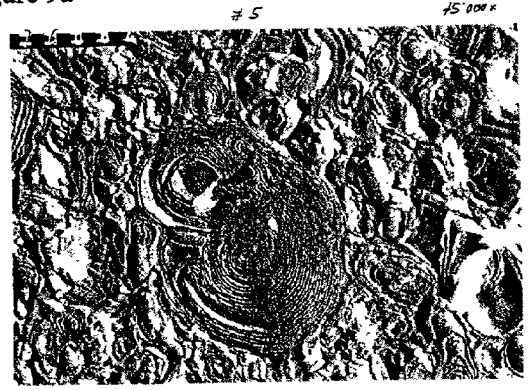
Figure 10:
FIG. 10 is a photograph of a model compound encapsulated within vesicles; the vesicles are contained in a dialysis tube and the model compound does not diffuse out of the membrane, demonstrating encapsulation.
Figure 11A:
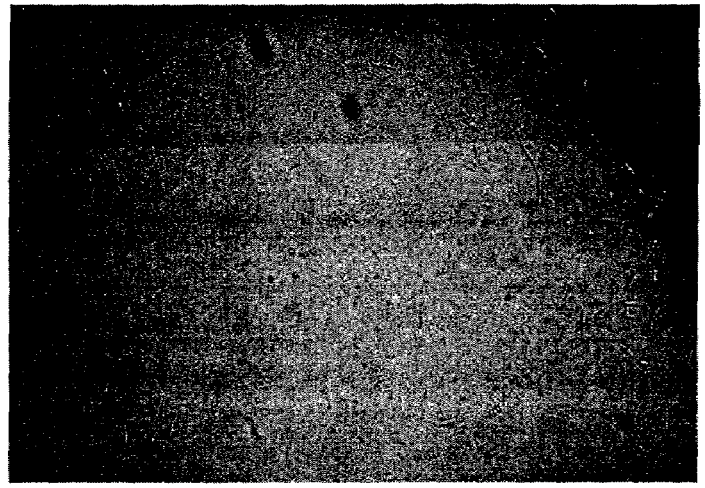
FIGS. 11A, 11B and 11C are light micrographs of cells (HFFs), treated (A) with vesicles containing an encapsulated model drug (AS-bFGF), (B) with non-encapsulated model drug, or (C) saline vehicle, each after 4 days culture following treatment.
Figure 11B:
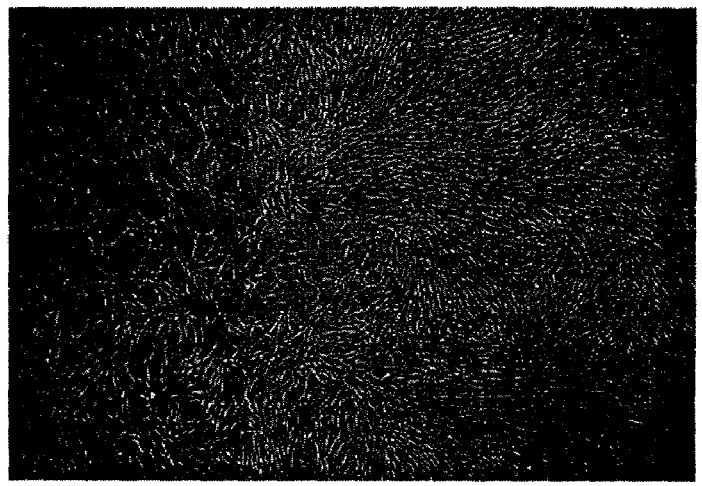
Figure 11C:
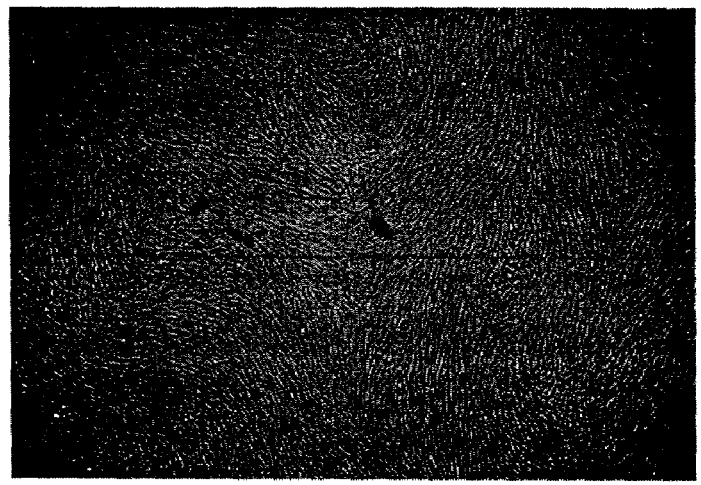
Figure 12:
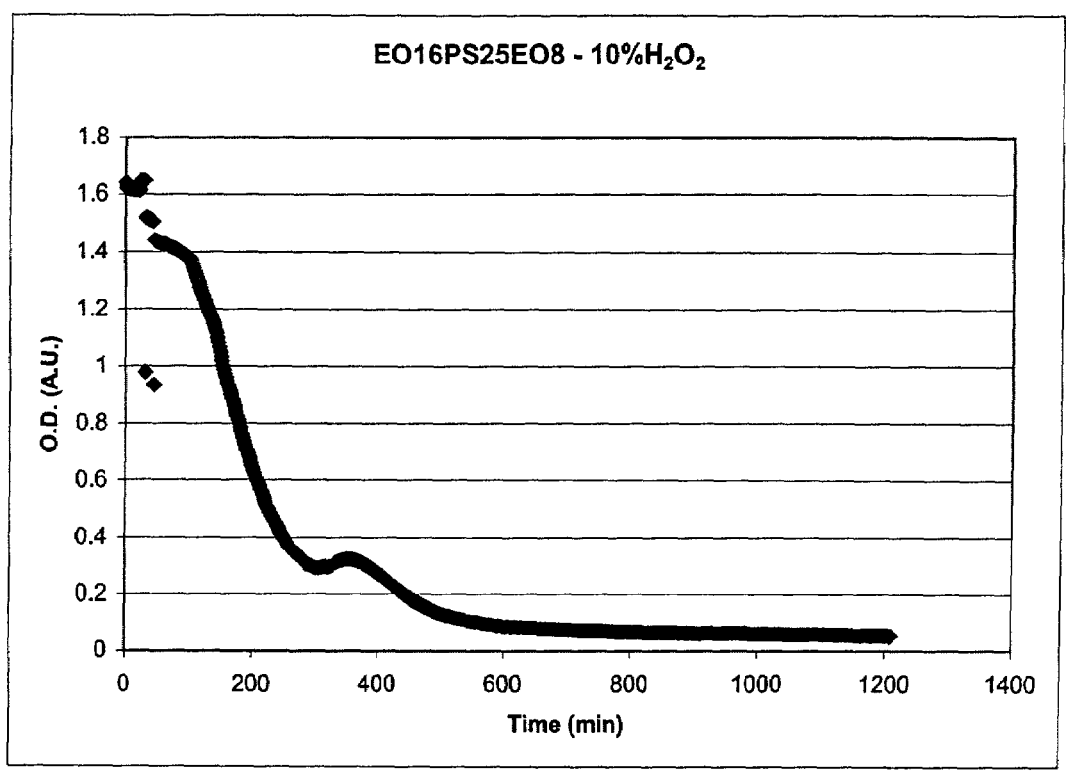
FIG. 12 is a graph showing the time dependence of the turbidity exhibited by a vesicular suspension of a triblock copolymer made of propylene sulfide and ethylene glycol in oxidizing environment (10% wt. $H_2O_2$).
Figure 13A:
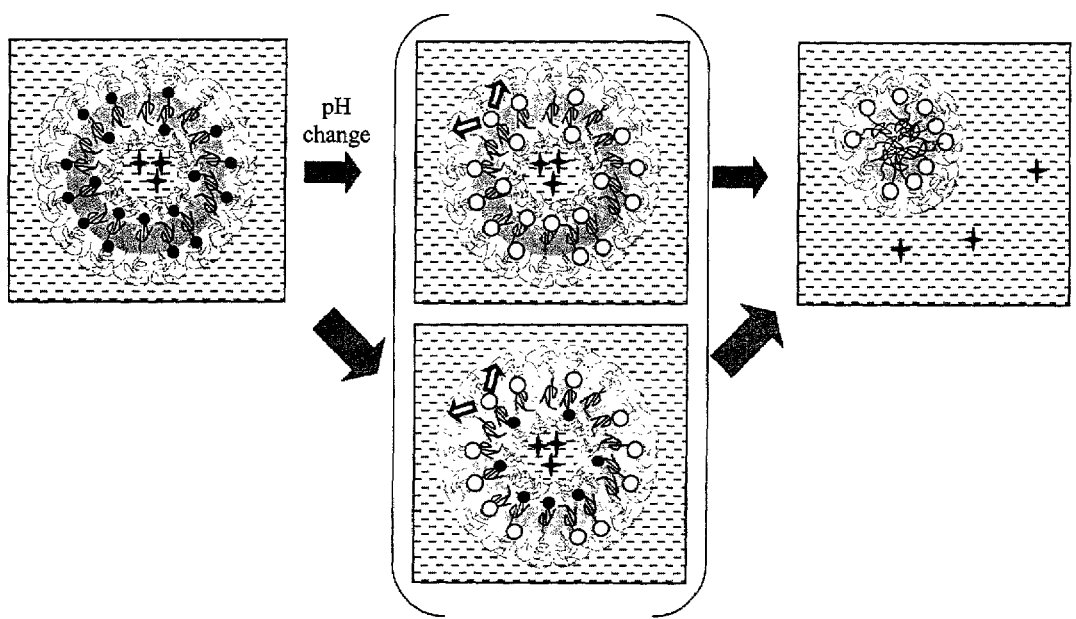
FIG. 13A illustrates pH sensitivity by pH-responsive moieties close to the hydrophobic block, in the case that both pH change diffuses into the internal cavity or not.
Figure 13B:
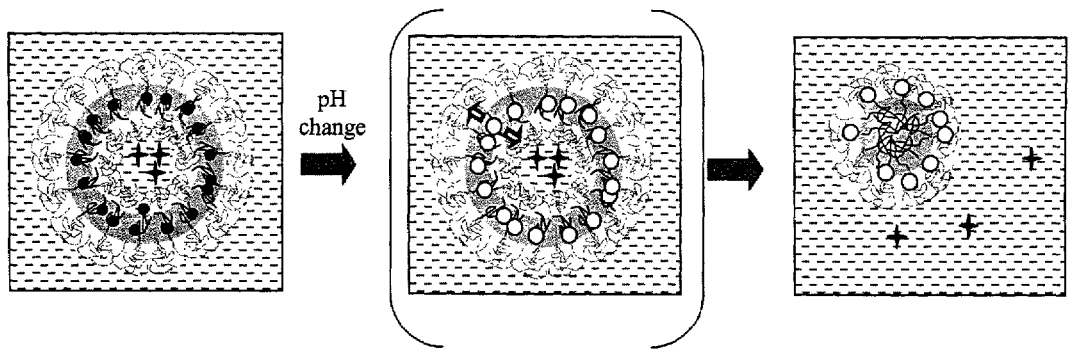
FIG. 13B illustrates pH sensitivity by pH-responsive moieties within the hydrophobic block.
Figure 13C:
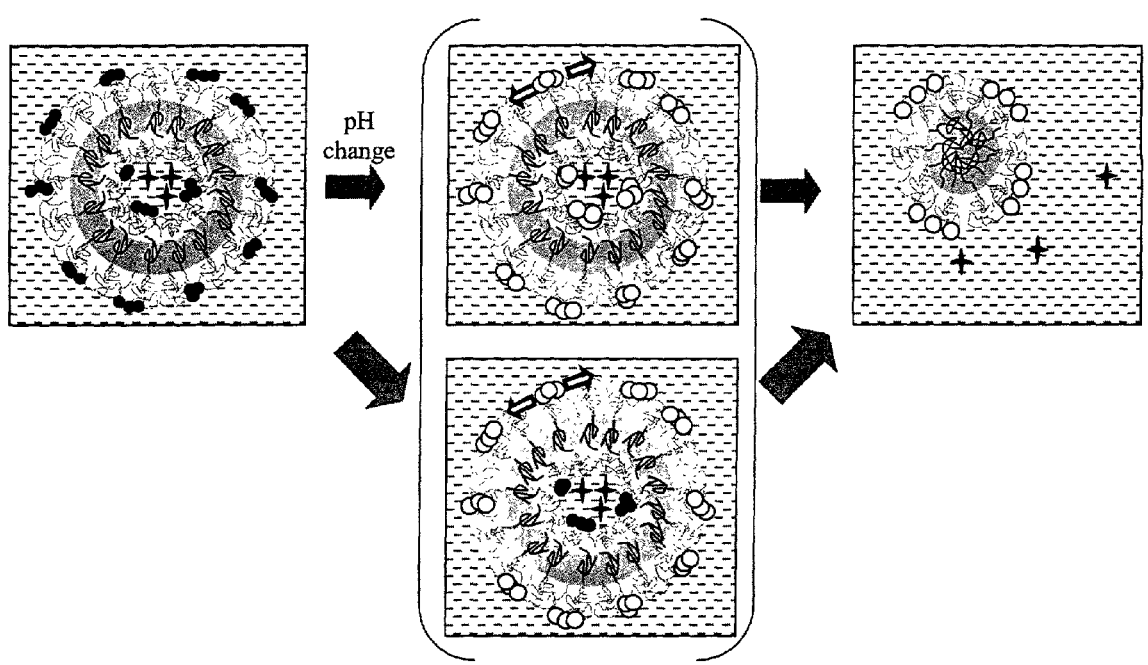
FIG. 13C illustrates pH sensitivity by pH-responsive moieties terminally attached in sequence to the hydrophilic block, in the case that both pH change diffuses into the internal cavity or not.

A triblock copolymer made of propylene sulfide and ethylene glycol (see Example 4) exhibited typical lamellar structures at the optical microscope with cross polarizers (FIG. 8); after sonication the water dispersion was freeze fractured: the corresponding TEM picture showed the formation of multilamellar vesicles coexisting with residual lamellar structures (FIGS. 9A and 9B) or with monolamellar vesicles (FIGS. 9A, 9B, and 9C).

EXAMPLE 6

Preparation of Vesicular Suspensions

Vesicular aggregates of amphiphilic substances can be prepared by dispersion of lamellar lyotropic aggregates or by solvent exchange from organic solutions. In the first case, the amphiphilic material is first exposed to water, in order to generate a layered lamellar phase, which is then disrupted by mechanical action and generates spherical vesicular structures. In the second case, a solution of the polymer in an organic water-soluble solvent is dropped into water, and the solvent exchange generates lyotropic structures. Substances to be encapsulated are, in the first case, dissolved in the water used for the film hydration and, in the second case, codissolved in the organic solvent. In both cases, the suspension is then extruded or filtered to reduce and homogeneize the diameter of vesicular structures and dialyzed in order to remove non-encapsulated material.

Preparation from Hydrated Films

A $CH_2Cl_2$ solution of a triblock copolymer made of a sequence 16:25:8 of monomeric units of, respectively, ethylene glycol, propylene sulfide, and ethylene glycol, was evaporated in a flask to yield a polymeric film. Water was added to produce a concentration of 2% of the polymer by wt. The mixture was then vortexed for 5 minutes and treated with 3 freeze-thaw cycles in liquid nitrogen. The suspension was finally filtered 10 times through polycarbonate membranes having a pore size of 100 or 200 nm. The hydrodynamic radii of the vesicles were characterized with dynamic light scattering.

Preparation from an Organic Solution

A tetrahydrofuran solution of a triblock copolymer made of a sequence 16:25:8 of monomeric units of, respectively, ethylene glycol, propylene sulfide, and ethylene glycol, is added dropwise into a dialysis membrane immersed in water. The final concentration of the polymer in the volume delimited by the membrane is estimated to be 3% by wt. After 1 day of dialysis, the suspension was purified with the same procedure as in the example of preparation from hydrated film.

EXAMPLE 7

Use of a Vesicle Suspension for Encapsulation of Nucleic Acid Derivatives

The same procedure as in the example for the preparation of vesicle suspensions from hydrated films was performed, but a $10^{-6}$ M solution of antisense (for b-FGF at position 57 to 63 in the 21 kD protein—196 AA) (Inoue et al., *Clinical Cancer Research* 2000, 6, 4422–4431) oligodeoxynucleotide (ODN) fluorescently labeled with fluorescein was used. Dialysis was performed until disappearance of fluorescein fluorescence (Ex. 497 nm, Em. 520 nm) in the dialysis solution.

EXAMPLE 8

Use of a Vesicle Suspension Encapsulating Nucleic Acid Derivatives for Gene Delivery to Cultured Cells Human Foreskin Fibroblasts were cultured on tissue culture polystyrene (TCPS) in a 24-well plate until 60% confluence. A 0.5% by wt. vesicular suspension was added in a volume appropriate to add 1 mg of ODN per well and was left in contact with the cell layer for 60 minutes. After washing, it was replaced with Dulbecco Eagle medium modified with 10% of fetal bovine serum and ABAM. Pictures of cells were taken at various time intervals and were compared with the administration of the same amount of non-encapsulated antisense ODN. The control experiments showed negligible effect on cell behavior, while the encapsulated material inhibited cell growth and proliferation.

All publications and patent applications mentioned in this specification are herein incorporated by reference to the same extent as if each independent publication or patent application was specifically and individually indicated to be incorporated by reference.

What is claimed is:

1. A method of synthesizing a block copolymer, said method comprising the steps of:
   (a) providing a first compound comprising a polymeric thiol precursor comprising a thiol bound to a protecting group;
   (b) generating a polymeric thiol from said first compound by removing said protecting group; and
   (c) initiating a polymerization of a second compound comprising an episulfide group with said thiol produced in step (b) thereby producing a block copolymer comprising a terminal thiol.

2. The method of claim 1, said method further comprising step (d) end-capping the product of step (c) with a third compound that comprises a group that is reactive to thiols thereby producing a block copolymer comprising at least three blocks.

3. The method of claim 1, said method further comprising step (d) using said terminal thiol from the product of step (c) in a second polymerization step.

4. The method of claim 1 or claim 2, wherein said first compound further comprises a hydrophilic polymer.

5. The method of claim 4, wherein said hydrophilic polymer is selected from the group consisting of poly(ethylene glycol), poly(ethylene oxide), poly(ethylene oxide)-co-poly(propylene oxide), poly(N-vinyl pyrrolidone), poly(ethyloxazoline), poly(acrylic acid), poly(ethylene-co-vinyl alcohol), poly(acrylamide), poly(N-alkyl or N,N-dialkylacrylamides), poly(acrylates), poly(peptides), and poly(saccharides).

6. The method of claim 5, wherein said hydrophilic polymer further comprises polar, ionic, or ionizable groups.

7. The method of claim 1 or claim 2, wherein said first compound further comprises polyether or a block copolymer, wherein at least one block comprises polyether.

8. The method of claim 7, wherein said polyether comprises a molecular weight of >300 Da and a terminal, electron-poor double bond.

9. The method of claim 7, wherein said polyether is poly(ethylene glycol).

10. The method of claim 1 or claim 2, wherein said first compound further comprises a peptidic sequence or a saccharidic sequence.

11. The method of claim 1 or claim 2, wherein said polymeric thiol precursor is selected from the group consisting of a thioester, a dithioester, a thiocarbamate, a dithiocarbamate, a thiocarbonate, a xanthate, and a trithiocarbonate.

12. The method of claim 1 or claim 2, wherein said first compound comprises a linear, star-shaped, or branched polymer with a thiol precursor at each end.

13. The method of claim 1 or claim 2, wherein said episulfide in step (c) comprises

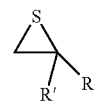

where R or R' comprises hydrogen, alkyl, hydroxyalkyl, alkoxyalkyl, phenyl, substituted phenyl, acyl, or carboxyalkyl.

14. The method of claim 2, wherein said third compound comprises polyether or a block copolymer, wherein at least one block comprises polyether and a Michael acceptor group or a leaving group capable of being displaced by a nucleophilic sulfur atom.

15. The method of claim 14, wherein said polyether comprises poly(ethylene glycol).

16. The method of claim 14, wherein said Michael acceptor is selected from the group consisting of acrylate, itaconate, acrylamide, itaconamide, maleimide, vinyl sulfone, quinone, multi-substituted quinone, fused quinone, vinyl pyridine, and vinyl pyridinium ion.

17. The method of claim 14, wherein said leaving group is selected from the group consisting of chloride, bromide, iodide, tosylate, mesylate, bromoacetate, iodoacetate, substituted and unsubstituted benzyl bromide, bromoacetamide, iodoacetamide, and triflate.

18. The method of claim 2, wherein said third compound comprises a compound having a low molecular weight and a group with Michael-type reactivity or a group capable of undergoing nucleophilic substitution.

19. The method of claim 18, wherein said third compound further comprises a functional group selected from the group consisting of peptide, ester, anhydride, and Schiff base, and acetal.

20. The method of claim 2, wherein said third compound further comprises a block copolymer comprising a group that undergoes hydrolytic degradation.

21. The method of claim 20, wherein said group is selected from the group consisting of aliphatic ester, anhydride, Schiff base, and acetal.

22. The method of claim 2, wherein said third compound is the product of step (c).

23. The method of claim 1 or claim 2, wherein said second compound comprises a compound selected from the group consisting of propylene sulfide, cyclohexene episulfide, and ethylene sulfide.

24. The method of claim 1 or claim 2, wherein the step (c) further comprises adding a fourth compound comprising an episulfide group.

25. The method of claim 24, wherein said third compound is added simultaneously with said second compound to produce a random copolysulfide.

26. The method of claim 24, wherein said third compound is added sequentially before or after said second compound to produce a block copolysulfide.

27. The method of claim 1 or claim 2, wherein the conversion of the thiol precursor to a thiolate in step (b) comprises a transesterification or transamidation reaction.

28. The method of claim 2, wherein said third compound is thiirane.

29. The method of claim 2, wherein said third compound further comprises a peptidic sequence or a saccharidic sequence.

30. The method of claims 10 or 29, wherein said peptidic or sacchardic sequence comprises a peptide or a saccharide that binds to an adhesion-promoting receptor.

31. The method of claim 30, wherein said peptidic sequence comprises RGD or YIGSR.

32. The method of claim 10 or 29, wherein said peptidic sequence comprises a proteolytically degradable sequence.

33. The method of claim 32, wherein said proteolytically degradable sequence comprises a substrate for a protease selected from the group consisting of plasmin, elastase, collagenase, and a matrix metalloproteinase.

34. The method of claim 2, wherein said third compound comprises a polymeric backbone identical in chemical nature to said first polymer.

35. The method of claim 2, further comprising a step (e) reacting a fourth compound with a terminal thiol of the product of step (d).

* * * * *

SEQUENCE LISTING

<160> NUMBER OF SEQ ID NOS: 1

```
<210> SEQ ID NO 1
<211> LENGTH: 5
<212> TYPE: PRT
<213> ORGANISM: Homo sapiens

<400> SEQUENCE: 1

Tyr Ile Gly Ser Arg
1               5
```